United States Patent [19]

Peault

[11] Patent Number: 5,147,784
[45] Date of Patent: Sep. 15, 1992

[54] T-LYMPHOCYTE PROGENITOR CELL ASSAY

[75] Inventor: Bruno Peault, Menlo Park, Calif.

[73] Assignee: SyStemix, Inc., Palo Alto, Calif.

[21] Appl. No.: 508,225

[22] Filed: Apr. 12, 1990

[51] Int. Cl.$^5$ .................. C12Q 1/04; C12Q 1/24; C12N 5/06; G01N 33/569
[52] U.S. Cl. ................... 435/7.24; 424/9; 435/30; 435/34; 435/240.2; 435/243
[58] Field of Search .................. 424/9; 435/7.24, 30, 435/34, 240.2, 243; 436/63

[56] References Cited

FOREIGN PATENT DOCUMENTS 0322240 6/1989 European Pat. Off. .
8912823 12/1989 World Int. Prop. O. .

OTHER PUBLICATIONS

J. Kurtzberg et al., Proc. Natl. Acad. SCI. U.S.A., 86, 7575-7579, 1989.
R. Scullay et al., *Immunol. Rev.*, 104, 81-120, 1988.

*Primary Examiner*—David Saunders
*Attorney, Agent, or Firm*—Bertram I. Rowland

[57] ABSTRACT

Methodology is provided for identifying the presence of human T-lymphocyte progenitor cells. Human thymus tissue is depleted of endogenous lymphold cells, repopulated with a human cellular composition which is HLA mismatched with the thymus tissue and implanted into a vascularizable site in an immunocompromised host. After at least about 2 weeks, the tissue may be assayed for the presence of the HLA mismatched T-lymphocytes as indicative of human T-lymphocyte progenitors in this cellular composition.

11 Claims, No Drawings

T-LYMPHOCYTE PROGENITOR CELL ASSAY

INTRODUCTION

1. Technical Field

The field of this invention is the assay of progenitors for human T-lymphocytes.

2. Background

The hematopoietic system is central to the well being of vertebrates. The system is extraordinarily complex and includes a varied number of cells of different morphology, function, and lifetime. The hematopoietic system is divided into several lineages including lymphoid, myeloid, and erythroid.

The lymphoid lineage is divided for functional reasons into two categories: B-lymphocytes and T-lymphocytes. The T-lymphocytes are further divided into a number of categories, two major divisions being helper cells, designated by having the surface marker CD4 and suppressor cells, designated by having the surface marker CD8. T-cells serve numerous functions in protecting a host from disease. The T-cells act to secrete lymphokines, to regulate B-lymphocyte proliferation, and to kill cancer cells and cells infected with virus, among other functions. Therefore, it is imperative that in providing a host with an immune system, the immune system be capable of producing T-lymphocytes. T-cells also act to attack transplanted organs and in the event of transplantation of bone marrow, where the HLA of the bone marrow is mismatched with the host, the presence of the mismatched T-lymphocytes can result in graft-versus-host disease.

There has been substantial effort in obtaining substantially pure compositions of early hematopoietic progenitor cells. Of particular interest has been the isolation in the mouse of what is referred to as the "stem" cell, which is capable of self regeneration and of differentiating into all of the different hematopoietic lineages. One of the difficulties in identifying human stem cells has been the lack of a convenient assay to determine whether the progenitor cell is capable of producing T-lymphocytes. It is therefore of interest to provide an assay whereby one could detect the ability of a human cell to produce T-lymphocytes, as well as other hematopoietic cells.

SUMMARY OF THE INVENTION

An assay for determining the ability of a progenitor human cell to produce T-cells is provided. The assay comprises depleting human thymus tissue of endogenous thymocytes, introducing the cellular sample to be tested into the thymocyte depleted tissue and, if not previously transplanted, transplanting the tissue into an immunocompromised, and thus graft-tolerant, animal host (lacking T-cells). After sufficient time for T-lymphocytes to arise from the progenitor cells, the thymus, peripheral blood, or other hematolymphoid tissue present may be assayed for the presence of donor-derived T-lymphocytes.

DESCRIPTION OF THE SPECIFIC EMBODIMENTS

In accordance with the subject invention, an assay is provided for the detection of the production of human T-lymphocytes from progenitor cells and the ability of the progenitor cells to self regenerate. The method has four stages: depletion of thymus tissue of endogenous thymocytes; thymus recolonization with the sample cell composition; if not previously transplanted, transplantation of the thymus tissue in an immunocompromised host; and assaying for the presence of mature T-lymphocytes after a predetermined time.

The thymus tissue which is used will be allogeneic with the sample cells to be assayed, normally being human thymus and human cells. The thymus tissue may be fetal tissue, neonatal tissue or adult tissue, preferably fetal tissue. Normally, the volume of the tissue required will be at least about 2 $mm^3$. Conveniently, it may be implanted with a 15 to 20 gauge needle or catheter. See, EPA 0 322 240, for a description of the transplantation of thymus tissue into an immunocompromised host.

The thymus tissue may be depleted in vitro of thymocytes by any convenient procedure. Various procedures include treatment with cytotoxic drugs, e.g. dideoxyguanosine, 5-fluorouracil, methotrexate, etc.; physical treatments such as irradiation, low temperature culture, or the like. All of these methods selectively eliminate hematopoietic cells, leaving the thymic microenvironment intact and able to support lymphopoiesis. Instead of an artificially depleted thymus, the epitheliomesenchymal "attractive" uncolonized thymus rudiment may be employed. Preferably, a more differentiated thymus is employed and either X-ray irradiation (500–1000 rad) or low temperature culture (25 to 30 degrees C., usually about 25 degrees C.) for approximately 3–7 days is employed, preferably the latter if the tissue has to be eventually engrafted.

Once the thymus tissue has been depleted, it can then be recolonized. The cellular composition used for reconstitution may be from a fetus, a neonate or more mature human host. The cellular composition may be from any lymphoid progenitor source, such as bone marrow, fetal liver, thymus, etc. The composition may have been subjected to prior treatment, such as selection for CD34+ cells, deletion of CD3, 4 or 8+ cells, or the like. The particular manner in which the cellular composition is pretreated will depend on the reason for the assay.

Various techniques may be employed for recolonization, such as "transfilter," or "hanging drop" culture or microinjection, microinjection being preferred.

The transfilter technique comprises associating a thymus fragment with a "donor" organ of thymocyte progenitors, e.g. fetal liver or bone marrow, on each side of a Nuclepore filter with a pore size (about 5 $\mu$m) which allows for cell trafficking. A chemotactically-induced cell migration occurs from the donor organ to the thymus. The medium employed for maintaining the tissue and cells is RPMI, 10% fetal calf serum. The system is maintained at a temperature of about 37° C. for 3 days. After such time, the thymus tissue is harvested and grafted into an immunodeficient animal host.

The hanging drop culture comprises culturing thymus tissue of about 1 to 5 $mm^3$ in a drop of medium hanging from the lid of a dish. The medium employed is RPMI, 10% fetal calf serum. The hanging drop allows for the conservation of the three-dimensional structure of the organ. The human cell progenitor compositions included in the culture medium can colonize the thymic explant and differentiate. It is found that a very limited number of donor cells can be used efficiently.

Preferably, microinjection is employed. Glass micropipettes are linked to an oil-filled micrometric screw-operated syringe. Cells are injected into the thymus fragments in a volume in the range of about 0.1 to 1 $\mu$l.

The cells are at a concentration of about 25 to $10^4$ cells/$\mu$l in RPMI medium.

Within 24 hours after repopulation, in vitro colonized fragments are implanted into an immunocompromised host. However less conveniently, the thymus may be engrafted prior to depletion and recolonization. Any convenient immunocompromised host may be employed, where the immunocompromised host is as a result of natural selection, breeding, or genetic engineering. The immunocompromised host should be substantially free of the T lymphoid lineage. Illustrative hosts include the beige mouse, the nude mouse, SCID mouse, etc. While other animals may be used, the mouse is found convenient as being small, easily handled, and can be maintained in large numbers.

Implantation may occur at any convenient site, such as the kidney capsule, popliteal fossa, mammary fat pad, particularly the fourth mammary fat pad of the mouse, or the like. Conveniently, it may be introduced into the kidney capsule. The cells which are employed for repopulation are HLA mismatched, so that their regeneration may be monitored as distinct from cells present in the human thymus. The particular manner of implantation is not critical and, as already indicated, has been described in the literature. The number of cells which are injected may be varied, depending upon the nature of the test. Thus, in testing for thymocyte progenitors, the higher percentage of the cell composition which is thymocyte progenitors, the fewer the cells that need to be introduced. After implantation, the animals may be sacrificed at intervals, usually beginning at least two weeks, preferably at least four weeks from the time of engraftment and the thymic tissue, peripheral blood, or other lymphoid organ may be assayed for the presence of HLA mismatched donor cells. Usually, the period of implantation will be for about 2 to 16 weeks, more usually for about 4 to 10 weeks.

The resulting cells may then by assayed for various T-cell specific or non-specific markers. T-cell specific markers include CD3, 4, 7, 8. The HLA Class I antigens are used to determine whether the cells are from the donor population or the endogenous thymus population. Other markers may be determined to determine the level of maturation of the T-cells. Normally, after 6 weeks, there is a substantial population of donor derived T-lymphocytes, of which a significant fraction expresses high levels of class I antigens. The presence of the T-cells demonstrates that the donor composition comprised T-cell progenitors.

The test can be used with any hematopoietic cell composition where there is an interest in determining the presence of human T-cell progenitors, particularly hematopoietic stem cells. Of particular interest are human fractions comprising CD34+, lineage marker minus (CD10-, CD19-, CD33-) and Thy-1+, desirably rhodamine-1,2,3 low, indicating the level of mitochondrial activity.

The following examples are offered by way of illustration and not by way of limitation.

EXPERIMENTAL

Human Thymus Low Temperature Organ Culture

Individual lobules from 19-21 week-old human fetal thymuses were dissected free of mesenchyme under a dissecting microscope and placed on sterile nitrocellulose filter squares (1 cm×1 cm) (Millipore) supported by absorbable gelatin sponges (Gelfoam, Upjohn), in 3.5 cm Petri dishes containing 2 ml of RPMI 1640, 10 percent heat inactivated fetal calf serum, penicillin-streptomycin. Cultures were incubated at 25 degrees C. in a 5% CO2 atmosphere.

Cell Microinjection

An oil-filled Hamilton syringe with a screw-operated plunger was used to inject through glass micropipettes cell suspensions (0.1-1 $\mu$l) into low temperature cultured thymus fragments. Cultures were incubated for 24 more hours at 37 degrees C. before grafting.

Grafting Into SCID Mice

In vitro colonized thymus fragments were inserted under the kidney capsule of Nembutal anesthetized SCID mice. Explants were grafted under the microscope with fine forceps.

Immunofluorescence Cell Analysis and Sorting

For chimerism analysis, engrafted mice were killed by cervical dislocation and human thymus fragments were dissected free of kidney tissue. Thymocytes were then mechanically dispersed and screened by two-color immunofluorescence, resuspended in the presence of propidium iodide and analyzed on a FACSscan fluorescence-activated cell analyzer (Becton-Dickinson). Phycoerythrin (PE) labeled anti-CD3, anti-CD4 and anti-CD8 monoclonal antibodies were purchased from Becton-Dickinson. Hybridomas secreting the following anti-MHC class 1 antibodies: BB7-2 (anti-A2), MA2.1 (anti-A2 and anti-B17), GAPA3 (anti-A3), W632 (anti-A,B, and C), BB7.1 (anti-B7), MB40-2 (anti-B7 and anti-B40) were obtained from the ATCC. Monoclonal antibodies were purified from ascitic fluid and directly labeled with fluorescein isothiocyanate (FITC). CD34+ cells were isolated on a FACStar fluorescence activated cell sorter from fresh human fetal liver or bone marrow cell suspensions using a monoclonal anti-CD34 IgM (available from Dr. Irving Bernstein).

After one month, the graft contains a detectable population of donor-derived T-cells, expressing low to medium levels of HLA class I antigens. When the graft has been extended for 6 weeks, a larger population of donor-derived T-lymphocytes is present, a fraction of which expresses high levels of class I antigens, which supports the presence of mature single positive cells.

Five of six grafts were found to contain CD34+ cell-derived T-lymphocytes (the negative thymus served as a good specificity control). Also grafted into SCID mice were thymuses that had been in vitro colonized in the transfilter and hanging drop systems; a donor-derived population of T-lymphocytes could be evidenced in most grafted mice.

| T Cell Repopulation of the Human Thymus Following In Vitro Colonization by Microinjection of Precursor Cell Populations and Regrafting into SCID Mice. | | |
|---|---|---|
| Precursor Cell Phenotype | Microinjected Cell Number | Repopulation* |
| FBM CD34+ | 10,000 | 9/12 |
| FBM CD34+ | 100 | 2/4 |
| FBM CD34+CD7- | 10,000 | 6 wks: 3/5  11 wks: ⅜ |
| FBM CD34+CD7+ | 10,000 | 6 wks: ⅜  11 wks: 0/3 |
| FBM CD34+Thy1+ | 10,000 | ⅜ |
| FBM CD34+Thy1- | 10,000 | 0/2 |
| FBM J143+Lin- | 10,000 | 12/14 |
| FMB Dexter Culture (6 wks) | 2,000 | 2/5 |

-continued

T Cell Repopulation of the Human Thymus Following
In Vitro Colonization by Microinjection of Precursor Cell
Populations and Regrafting into SCID Mice.

| Precursor Cell Phenotype | Microinjected Cell Number | Repopulation* |
|---|---|---|
| CD34+ | | |

*Numbers represent the number of mice showing reconstitution by donor cells/total number of mice analyzed.
FBM — fetal bone marrow: J143 - mAb to Class II Ag.
Lin — lacking CD3, 8, 10, 19, 20 and 33

It is evident from the above results that a sensitive accurate assay is provided for detecting the presence of T-lymphocyte progenitor cells from a cell population suspected of containing T-lymphocyte progenitors. Thus, one can now study the presence of progenitor cells for T-lymphocytes, the effect of factors on the differentiation and expansion of T-lymphocytes, and provide for the expansion of T-lymphocytes from a cell population having T-cell progenitors.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for determining the presence in a cellular composition of human progenitor cells to T lymphocytes, said method comprising:
   depleting human thymus tissue of lymphoid cells;
   repopulating said thymus tissue with said cellular composition, wherein said cells of said cellular composition are HLA mismatched with said thymus tissue;
   implanting said repopulated thymus tissue in an immunocompromised non-human mammalian host at a site where said tissue is vascularized, when said thymus tissue has not been previously transplanted; and
   after a predetermined time period, assaying for the presence of T lymphocytes having the HLA of said cellular composition.

2. A method according to claim 1, wherein said host is murine.

3. A method according to claim 2, wherein said murine host is a scid/scid mouse.

4. A method according to claim 1, wherein said thymus is fetal thymus.

5. A method according to claim 1, wherein said cellular composition is concentrated for CD34+ cells.

6. A method for determining the presence in a cellular composition of human progenitor cells to T lymphocytes, said method comprising:
   depleting human fetal thymus tissue of lymphoid cells;
   repopulating said thymus tissue with said cellular composition, wherein said cells of said cellular composition are HLA mismatched with said thymus tissue and concentrated for CD34+;
   implanting said repopulated thymus tissue in an immunocompromised mouse host at a site where said tissue is vascularized; and
   after a predetermined time period, assaying for the presence of T lymphocytes having the HLA of said cellular composition.

7. A method according to claim 6, wherein said site is the kidney capsule.

8. A method according to claim 6, wherein said repopulation is by microinjection.

9. A method according to claim 8, wherein said cellular composition is from a fetus.

10. A method according to claim 8, wherein said cellular composition is from a human host which is at least of an age of neonate.

11. A method according to claim 6, wherein said depleting is at a reduced temperature in the range of about 25 to 30 degrees centrigrade.

* * * * *